(12) United States Patent
Djavakhia et al.

(10) Patent No.: US 6,528,480 B1
(45) Date of Patent: Mar. 4, 2003

(54) PROTEIN WITH PLANT PROTECTING PROPERTIES

(75) Inventors: Vitali Djavakhia, Mozhaiskoe shosse, 6-41, Bolshie Viazemi, Odintsovo District, Moscow Region (RU), 143050; Natalia Batchikova, Tikankatu 28 C 13, Turku (FI), FIN-20610; Timo Korpela, Kasarminkatu 5 as 8, Turku (FI), FIN-20500; Radii Khomutov, Profsouznaia str. 43-I-46, Moscow (RU), 117420; Oleg Nikolaev, Institute str., 16-11, Bolshie Viazemi, Odintsovo District, Moscow Region (RU), 143050

(73) Assignees: Natalia Batchikova, Turku (FI); Vitali Djavakhia, Moscow (RU); Radii Khomutov, Moscow (RU); Timo Korpela, Turku (FI); Oleg Nikolaev, Moscow (RU)

( * ) Notice: Subject to any disclaimer, the term of this patent is extended or adjusted under 35 U.S.C. 154(b) by 0 days.

(21) Appl. No.: 09/000,476

(22) PCT Filed: Aug. 2, 1996

(86) PCT No.: PCT/FI96/00428

§ 371 (c)(1),
(2), (4) Date: Aug. 20, 1998

(87) PCT Pub. No.: WO97/05165

PCT Pub. Date: Feb. 13, 1997

(30) Foreign Application Priority Data

Aug. 2, 1995 (FI) ................................................ 953688

(51) Int. Cl.$^7$ .......................... C12N 1/00; C12N 1/20; C07H 17/00; C07K 14/00
(52) U.S. Cl. ................... 514/2; 424/93.1; 424/93.461; 424/195.1; 424/197.1; 424/405; 435/252.3; 435/252.5; 435/267; 435/320.1; 435/325; 435/832; 530/350; 536/23.1
(58) Field of Search .......................... 424/93.1, 93.461, 424/195.1, 197.1, 405, 320.1, 325, 252.3; 435/252.5, 267, 832; 514/2; 530/350; 536/23.1

(56) References Cited

U.S. PATENT DOCUMENTS 5,198,350 A * 3/1993 Horisberger et al. .......... 435/91
5,470,971 A 11/1995 Kondo et al. ............... 526/23.7
5,760,189 A * 6/1998 Vicik et al. .................. 530/412
5,817,500 A * 10/1998 Hansen et al. ............... 435/200

FOREIGN PATENT DOCUMENTS

WO    WO 89/04868 A1    6/1989    ............ C12N/5/00

OTHER PUBLICATIONS

Chilcott et al., "Comp. Tox. of B.T. var Israel. Crystal Prot in vivo & in vitro", J. of Gen'l Microb., 134, 2551–2558, 1998.*

Baulcombe, D., "Novel strategies for engineering virus resistance in plants," *Current Opinion in Biotechnology*, 5(2):117–124 (1994).

Bradford, M. "A Rapid and Sensitive Method for the Quantitation of Microgram Quantities of Protein Utilizing the Principle of Protein–Dye Binding," *Analytical Biochemistry*, 72:248–254 (1976).

de Barjac, H. et al., "A Classification of Strains of *Bacillus thuringiensis* Berliner with a Key to Their Differentiation," *Journal of Invertebrate Pathology*, 11:335–347 (1968).

Jones et al., "The Cold–Shock Response: A Hot Topic," *Chemical Abst.*,120:265378g (1994).

Krieg, A., "A Taxonomic Study of *Bacillus thuringiensis* Berliner," *Journal of Invertebrate Pathology*, 12:366–378 (1968).

Laemmli, U.K., "Cleavage of Structural Proteins during the Assembly of the Head of Bacteriophage T4," *Nature*, 227:680–685 (1970).

Latterell, F.M. et al., "Co–ordination of Effort to Establish an International System for Race Identification in *Piricularia oryzae*," in *The Rice Blast Diease*, Baltimore, Maryland, The John Hopkins Press, pp. 257–274 (1964).

Lee, S.J. et al., "Family of the major cold–shock protein, CspA (CS7.4), of *Escherichia coli*, whose members show a high sequence similarity with the eukaryotic Y–box binding proteins," *Molecular Microbiology*, 11(5):833–839 (1994).

Pappu, H.R. et al., "Application of Recombinant DNA Technology to Plant Protection: Molecular Approaches to Engineering Virus Resistance in Crop Plants," *World J. Microbiol. & Biotech.*, 11:426–437 (1995).

Schroeder, K. et al., "Mapping of the *Bacillus subtilis* cspB gene and cloning of its homologs in thermophilic, mesophilic and psychrotrophic bacilli," *Chemical Abst.*, 120:262522p (1994).

Schröder, K. et al., "Mapping of the *Bacillus subtilis* cspB gene and cloning of its homologs in thermophilic, mesophilic and psychrotrophic bacilli," *Gene*, 136:277–280 (1993).

Stermer, B.A. and Hammerschmidt, R., "Heat Shock Induces Resistance to *Cladosporium cucumerinum* and Enhances Peroxidase Activity in Cucumbers," *Physiological Plant Path.*, 25:239–249 (1984).

(List continued on next page.)

*Primary Examiner*—Karen Cochrane Carlson
*Assistant Examiner*—Deborah K. Ware
(74) *Attorney, Agent, or Firm*—Marshall, Gerstein & Borun (57) ABSTRACT

An MF2 protein having the amino acid sequence depicted in SEQ. ID. NO. 2, itself or as a part of any larger protein, or a functional derivative thereof having antiviral and/or antifungal activities, which protein is derivable from *Bacillus thuringiensis*. The invention also concerns a method for isolating and purifying the protein from bacterial cells expressing said protein, recombinant expression of the MF2 gene in a host cell, and the use of said protein as plant protectant.

41 Claims, 4 Drawing Sheets

OTHER PUBLICATIONS

Willimsky, G. et al., "Characterization of cspB, a *Bacillus subtilis* Inducible Cold Shock Gene Affecting Cell Viability at Low Temperatures," *Chemical Abst.*, 119:64390k (1993).

Willimsky, G. et al., "Characterization of cspB, a *Bacillus subtilis* Inducible Cold Shocks Gene Affecting Cell Viability at Low Temperatures," *J. Bacteriology*, 174(20):6326–6335 (1992).

Holt et al., (Eds.) *The Shorter Bergey's Manual of Determinative Bacteriology*, 8th Ed., Williams and Wilkins Co., Baltimore, MD, 356 pp. (1977) (English version of 1980 Russian Edition) pp. 201–202, 204.

* cited by examiner

```
         10         20         30         40         50         60
          .          .          .          .          .          .
ATGCAAACAGGTAAAGTTAAATGGTTCAACAGCGAAAAAGGTTTCGGTTTCATCGAAGTT
MetGlnThrGlyLysValLysTrpPheAsnSerGluLysGlyPheGlyPheIleGluVal
                                          .
                                         10                    20

70         80         90        100        110        120
          .          .          .          .          .          .
GAAGGTGGAGACGATGTATTCGTTCACTTCTCAGCTATCCAAGGTGACGGATTCAAAACT
GluGlyGlyAspAspValPheValHisPheSerAlaIleGlnGlyAspGlyPheLysThr
                             .                                  .
                            30                                 40

130        140        150        160        170        180
          .          .          .          .          .          .
TTAGAAGAAGGTCAAGAAGTTTCTTTCGAAATCGTTGAAGGTAACCGTGGACCACAAGCT
LeuGluGluGlyGlnGluValSerPheGluIleValGluGlyAsnArgGlyProGlnAla
                             .                                  .
                            50                                 60

190        200
          .          .
GCTAACGTTACAAAAAACTAA
AlaAsnValThrLysAsnEnd
    .
   66
```

FIG. 6

PROTEIN WITH PLANT PROTECTING PROPERTIES

This application is a United States national filing pursuant to 35 U.S.C. §371 of International Application No. PCT/FI96/00428, filed Aug. 2, 1996, which claims priority from Finnish Patent Application No. 953688, filed Aug. 2, 1995.

FIELD OF THE INVENTION

This invention relates to biotechnology and more particularly to the biological protection of plants against viral and fungal infections. The invention concerns a new protein which was isolated from the bacterium *Bacillus thuringiensis* and which can be used for the biological control of plant diseases and also as a source for making transgenic plants with multiple resistance to different plant viruses and phytopathogenic fungi.

BACKGROUND OF THE INVENTION

Less than 12 years ago biologists created the first transgenic plants. Since then, researchers have applied genetic engineering to more than 50 plants species. The technique has helped investigators gain critical insight into fundamental processes that govern the development of plants, and the first such genetically modified plants have been commercially introduced. Although genetic engineering is more complex than traditional plant breeding practices, it is just as safe. In both methods, new DNA enters the plant's genome and is stably maintained and ex-pressed.

About 4 years ago a US National Academy of Sciences report concluded that "crops modified by molecular and cellular methods should pose risks no different from those modified by classical genetic methods for similar traits". At about the same time the White House stated that genetically engineered products should not be subject to additional federal regulations, because they do not pose any unreasonable risk.

One of the most promising traits gene transfer offers is resistance to diseases. Exciting results have been achieved in creating plants resistant to viruses, an important matter because currently no direct way to treat virus-infected plants exists. Most infections reduce crop yield, but occasionally some prove to be catastrophic. Good farming practices, such as rotating crops and removing weeds and using meristem culture, can contain viruses, but only partially. Insecticides are sometimes used to control the pests responsible for transmitting viruses but in very specific and limited cases.

Investigators of Monsanto and some other companies constructed a vector to introduce and express phytovirus genes in different plants. The experiments with plants so modified have shown that the expression of the virus genes confers resistance only to the same virus strains. It means that plants with such specific resistance may have limited practical application. Nevertheless, workers have now engineered effective tolerance to more than a dozen different plant viruses in a broad range of crop species /Baulcombe, 1994/. But in each of these cases the problem of limited resistance is always a concern with the practical application of these plants. One of the possible ways of solving this problem is to use genes of factors which induce multiple resistance of plants.

SUMMARY OF THE INVENTION

The object of the invention is a protein MF2 or a functional derivative thereof with a new structure that can induce resistance of plants to viral and fungal infections. The structure of the protein is depicted in SEQ. ID. No. 2.

The invention also concerns an isolated DNA sequence encoding the said protein, the DNA having the sequence depicted in SEQ. ID. No. 1, as such, or as a part of any DNA sequence, or a fragment thereof, or it is a DNA sequence which has degenerate codons with respect to the DNA sequence defined above.

The invention also concerns a method of isolating and purifying the protein MF2 from bacterial cells expressing the said protein.

A further object of the invention is the use of the protein, or of compositions containing the same, as a plant protectant, for inducing resistance of plants to viral and fungal phytopathogens.

DETAILED DESCRIPTION OF THE INVENTION

We have isolated from a microorganism, *Bacillus thuringiensis*, a factor MF2 in homogenic consistency which in low concentration induces multiple resistance of different plants to viral infections. The said factor MF2 is a thermostable, low molecular weight protein (7239 daltons). The factor is obviously a new protein for we failed to find a full homology through a thorough computerised search of protein databases. The protein appears to be highly homological to cold shock proteins from Bacillus species /Schröder et al., 1993, Willimsky et al., 1992/ and less homological to cold shock proteins from *E coli* /Lee et al., 1994/.

The protein according to the invention can be used in solving phytopathological problems. Preparations of the thermostable protein can be used in meristem virus-free culture technology of plants. It seems that the use of this ecologically pure non-phytotoxic substance could be effective for obtaining virus-free clones of various agricultural plants. A knowledge of the structure of this protein provides the possibility for making gene constructs for obtaining transgenic plants resistant to viral and other diseases.

There art some advantages of such transgenic plants. It is known that transgenic plants that contain parts of viral genome have, as a rule, specific resistance to this particular virus. The microorganism used according to the invention does not have any relations to phytopathogenic viruses which occur in nature and we have shown that the protein induces non-specific resistance of tobacco plants to Tobacco Mosaic Virus (TMV) as well as to Potato Virus X (PVX).

At the same time, treatment of potato plants with MF2 has led to the induction of resistance against late blight disease *Phytophtora infestans*. It was also shown that the MF2 protein can induce resistance of rice plants against rice blast disease, *Pyricularia oryzae*.

The DNA sequence coding MF2 protein can be cloned into any cloning and/or expression vector for any organism, from bacterium to higher eukaryotes, including plants, with the help of commonly used genetic engineering methods, as described, for example in Sambrook et al. (1989).

We have also cloned the gene encoding said protein and determined the sequence of this gene. We have also determined the amino acid sequence from the N-terminus of the protein MF2.

We have further expressed the MF2 gene in *E. coli*. Expression of the recombinant MF2 in other bacteria can be achieved using other vectors and promoters including commercially available ones, for example, plasmids containing tac-, trp-promoters or promoters of bacteriophage origin $P_L$, T3, T7 etc). The MF2 can be expressed as chimeric protein by fusion of the MF2 gene with a gene of another bacterial protein.

For expression of the recombinant MF2 in other organisms suitable elements of genetic control and protein synthesis need to be considered. For example, to introduce the MF2 gene into yeast, plasmids which replicate autonomously can be used as well as integrating plasmids, centromere plasmids etc. To direct expression of the MF2 gene promoters of various yeast proteins may be included into vector (acid phosphatase (PHO5), alcohol dehydrogenase (ADH) glyceraldehyde-3'-phosphate dehydrogenase (GAPDH) etc). For expression of MF2 gene in plants plasmids as $T_i$ of different types or $R_i$ may be used. Among promoters suitable for this purpose are the promoter of the cauliflower mosaic virus 35S RNA gene (35S promoter) and the 2'-promoter derived from the 2' gene of the T-DNA of the $T_i$ plasmid.

The present invention deals with an earlier unknown protein structure, having documented activity against different phytoviruses and phytopathogenic fungi. The use of the gene of this protein could dramatically shorten the development time of new agricultural trarsgenic plant varieties with permanent and stable multiple resistance against economically important phytopathogenic viruses and fungi.

The cultivation of transgenic plants constructed with the gene encoding this protein could replace the very expensive hand-made technology of meristem culture and, in some cases, it could replace the use of chemical insecticides against virus transmitting pests and chemical fungicides against phytopathogenic fungi.

A further object of the present invention is a method for isolating and purifying the protein MF2 from bacterial cells expressing said protein, which method comprises (a) extracting the bacterial cells with an appropriate buffer solution by heating to an elevated temperature, preferably on a boiling water bath, in order to eliminate the main part of the temperature sensitive substances from the extraction medium, (b) precipitating the crude polypeptide at low temperature with an appropriate precipitant to eliminate lower molecular weight organic substances from the protein fraction, (c) fractionating a suspension of the precipitate through an anion exchange chromatography column, and collecting fractions with antiviral or antifungal activity, (d) performing PAGE electrophoresis of the protein fractions with antiviral or antifungal activity, and (e) recovering the protein eluted from the gel.

In the heating step the bacterial cells, such as *Bacillus thuringiensis*, are preferably extracted with a potassium-phosphate buffer at pH 7.4 containing EDTA, PMSF (phenyl methyl sulphonyl fluoride), ME (beta-mercaptoethanol) and Triton X-100 (polyoxyethylene ether). The precipitation is preferably carried out at a temperature of 2 to 6° C. with cool chloroform and/or propanol and/or ammonium sulphate solution.

A further object of the invention is the use of the protein MF2 or of a composition containing said protein MF2 as well as carriers and adjuvants known in the art, as a plant protectant. We have shown plant protectant activity especially on tobacco plants against Tobacco Mosaic Virus and Potato Virus X. We have also shown protectant activity on potato plants against *Phytophtora infestans* and on rice plants against *Pyricularia oryzae*.

In the following tests the *Bacillus thuringiensis* strain VNPB-17-3 (All-Russian Microbiological Collection) was used which is one of the bacterial strains isolated from the leaves of potato plant in a field of a farm in the Odintsovo district of Moscow region.

Cultural and morphological properties of strain VNPB-17-3: The cells are rod-shaped (1.0–1.2×3–5 nm), majority motile, flagella typically lateral. Heat-resistant endospores formed; not more than one in a sporangial cells. Gram-positive. Spores have elliptical form. Dominant position of spores are central. Products of action on glucose (but not on arabinose, xylose or mannitol when glucose is replaced by these substances) are: acid, when cultivated on the following medium (grams per liter):$(NH_4)_2$ $HPO_4$, 1.0; KCl, 0.2; Mg $SO_4 \times 7H_2O$, 0.2; yeast extract, 0.2; agar, 15; bromcresol purple, 0.008; glucose (added after sterilization), 5; used as slants. Another product of action on glucose is acetoin, when cultivated on the following medium (gram per liter):protease peptone, 7; glucose, 5; NaCl, 5. Optimal temperature of growth is 30° C., minimum is 10° C. and maximum 45° C. Optimal pH is 7.0. Bacterium can fix atmospheric nitrogen. Bacterium is catalase-positive organism. Tyrosine could not be decomposed by this strain. Data of the morphological, cultural, physiological and biochemical analysis have permitted us to conclude that the isolated bacterial strain belongs to *Bacillus thuringiensis* species (The shorter Bergey's Manual of Determinative Bacteriology, 1980; de Barjac & Bonnefoi, 1967; Krieg A., 1968).

Antiviral Activity of a Boiled Extract of *B. thuringiensis* Strain VNPB-17-3

EXAMPLE 1

Preparation of a Boiled Extract of *B. thuringiensis* Protein

Bacterial cells were collected by centrifugation at 6000 rpm during 20 min (Sorvall-RC28S centrifuge, rotor GS-3) and washed twice with distilled water. The material was resuspended in 100 ml of 50 mM potassium-phosphate buffer, pH 7.4, containing 4 mM EDTA, 1 mM PMSF, 1% beta-mercaptoethanol (ME) and 0.1% Triton X-100. The bacterial cells were disrupted by heating on a boiling water bath during 20 min and centrifuged at 6000 rpm, 20 min.

All further steps of purification were made at low temperature (2–6° C.). The supernatant was treated with one volume of cold chloroform and centrifuged at 3000 rpm during 20 min and then 15 min at 20000 rpm (Sorvall-RC28S centrifuge, rotor F26/50). The precipitate was removed and the material was treated with 5 volumes of cold propanol. The mixture was stored overnight at −20° C. and then centrifuged 15 min at 20000 rpm. The supernanant was lyophilised.

The following examples serve to illustrate certain methods of carrying out our invention. A boiled extract of the *B.*

*thuringiensis* strain VNPB-17-3 was used in these experiments. This preparation was obtained by the method described above.

EXAMPLE 2

Figure 1:
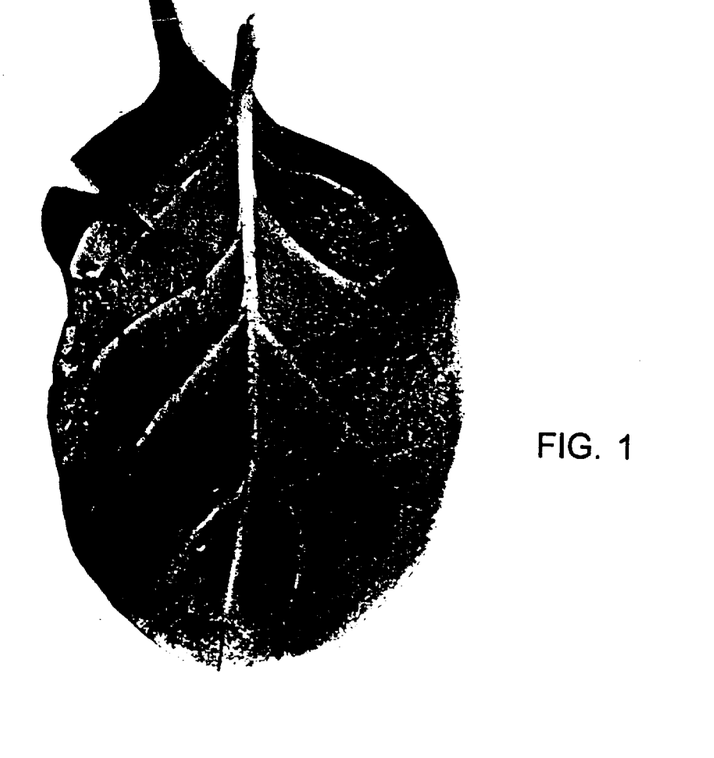
FIG. 1 shows the antiviral activity of the protein factor isolated from *Bacillus thuringiensis*.

The Protective Properties of MF2 Against Tobacco Mosaic Virus (TMV) on Tobacco Plants Tobacco plants (*Nicotiana tabacum* var. Virginia and *Nicotiana glutinosa*) were grown to a stage of six leaves (for about 3 weeks) in pots with soil in a climatic chamber at RH (relative humidity) 60% and temperature of 24° C. during light and dark periods (12 h each). Leaves of tobacco plants were inoculated with a paintbrush using carborundum as an abrasive. Each half of a tobacco leaf of 3-weeks-old plants were rubbed (with carborundum) with 0.3 ml of boiled extract of *B. thuringiensis* (50 μg/ml of lyophilised extract in 10 mM K-phosphate buffer, pH 7.0, 4 mM EDTA, 1 mM PMSF, 1 mM dithiothreitol). The opposite side of the same leaves were treated with buffer (control). Two days later both sides of the same leaves were rubbed with a Tobacco Mosaic Virus suspension (200 μg/ml, in 10 mM K-phosphate buffer, pH 7.0, 0.3 ml/half of leaf). Typical symptoms of disease development (left part of leaf) and antiviral activity of isolated MF2 factor (right part) are shown in FIG. 1.

The amount of infective lesions on each half leaf were calculated after 3 days. Disease development (%) was measured as a ratio of number of lesions in test to control. The results are shown in Table I. The boiled extract from *B. thuringiensis* has shown protective effect on tobacco plants from TMV-infection.

TABLE I

Antiviral activity of boiled bacterial extract (MF2) from *B. thuringiensis*
Number of lesions on: treated by MF2 half of leaves/untreated half of leaves

| *N. tabacum* var. Virginia | | | *N. glutinosa* | | |
|---|---|---|---|---|---|
| 20/69 | 15/101 | 25/78 | 5/23 | 0/8 | 6/15 |

EXAMPLE 3

Protective Properties of MF2 Against Potato Virus X (PVX) on Tobacco Plants

Four 3-weeks-old tobacco plants (*Nicotiana tabacum*, varieties Xanthy and Virginia) were used for each plant variety. The third and fourth (counted from the top) leaf of the plants were rubbed with 0.5 ml of MF2 extract (50 μg/ml lyophilzed extract precipitate was dissolved in 10 mM $KH_2PO_4$-buffer, pH 7). Four control plants of each variety were treated with the same buffer without the extract. After one day, all plants were inoculated with Potato Virus X (PVX). PVX was used as a leaf extract from fully PVX infected potatoes, stored frozen at −70° C.

Two weeks after the inoculation, PVX was tested in all the treated leaves using standard enzyme-linked immunosorbent assay (ELISA). The ELISA-tests were carried out using a PVX ELISA kit (All-Russian Potato Research Institute, Malakjovka, Moscow region). The absorbances were measured using 0.1% leaf juice according to standard assay procedures. The results of these experiments are presented in Table 2. These results showed a high level of protective activity of MF2 against PVX on tobacco plants.

TABLE 2

Antiviral activity of MF2 against PVX on tobacco plants

| | Absorption at 490 nm | |
|---|---|---|
| Variants of experiment | var. Xanthy | var. Virginia |
| PVX + buffer | 2.47 ± 0.05 | 2.74 ± 0.15 |
| FVX + MF2 | 0.15 ± 0.07 | 0.09 ± 0.03 |
| Negative control | 0.04 ± 0.02 | 0.03 ± 0.01 |
| Positive control | 2.53 ± 0.14 | 2.63 ± 0.15 |

Isolation and Purification of MF2 from *Bacillus thuringiensis*

EXAMPLE 4

Disruption of Bacterial Cells and Fractionation with Organic Solvents

Bacterial cells were collected by centrifugation at 6000 rpm during 20 min (Sorvall-RC28S centrifuge, rotor GS-3) and washed twice with distilled water. The material was resuspended in 100 ml of 50 mM potassium-phosphate buffer, pH 7.4, containing 4 mM EDTA, 1 mM PMSF, 1% beta-mercaptoethanol (ME) and 0.1% Triton X-100. The bacterial cells were disrupted by heating on a boiling water bath during 20 min and centrifuged as described above. All further steps of purification were made at low temperature (2–6° C.). The supernatant was treated with one volume of cold chloroform and centrifuged at first at 3000 rpm during 20 min and then 15 min at 20000 rpm (Sorvall-RC28S centrifuge, rotor F-28/50). The precipitate was removed and the material was treated with 5 volumes of cold propanol. The mixture was stored overnight at −20° C. and then centrifuged for 15 min at 20000 rpm.

EXAMPLE 5

Anion Exchange Chromatography

Figure 2:
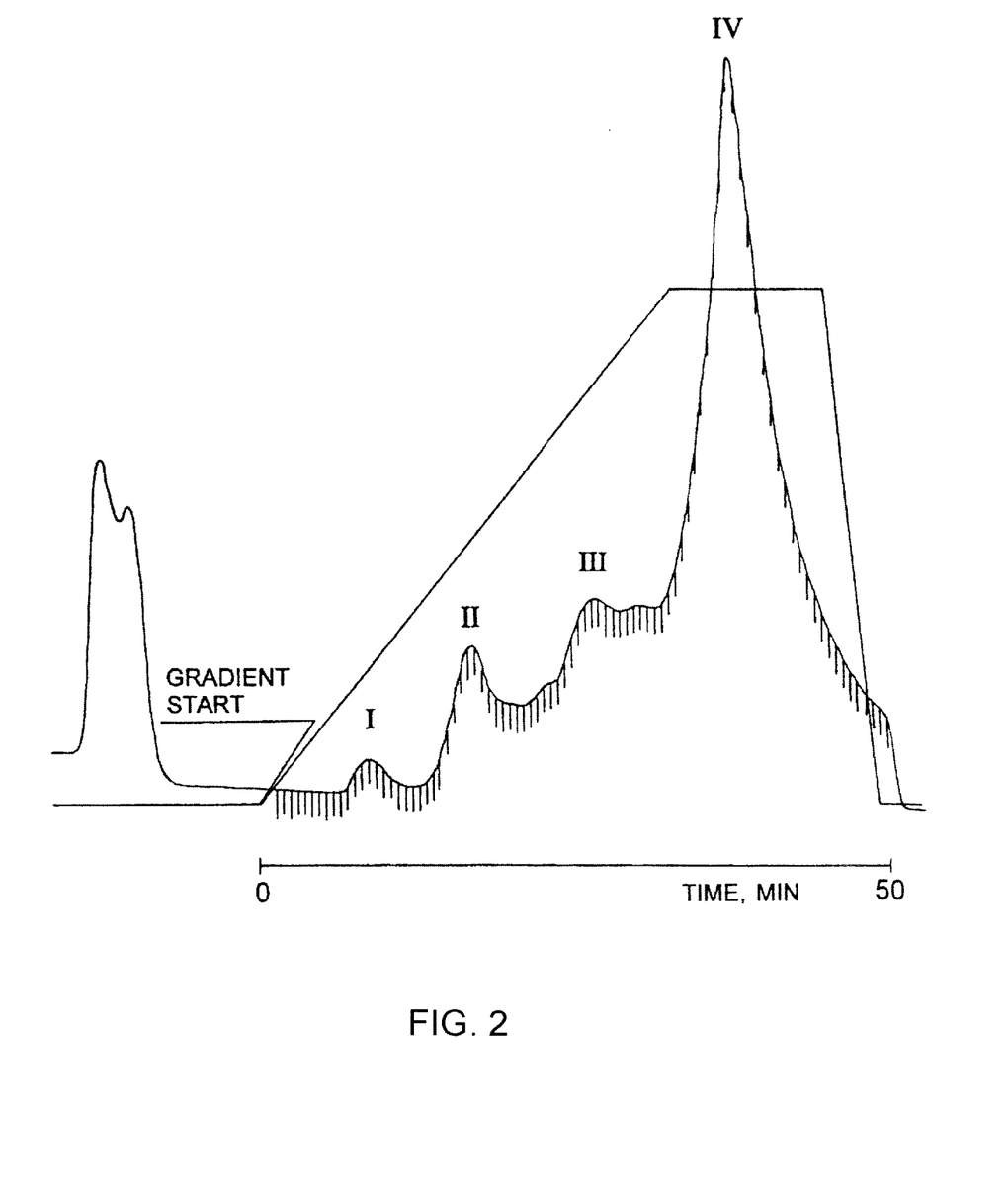
FIG. 2 shows purification of the antiviral factor on DEAE Sepharose.

The precipitate was suspended in 250 ml of 20 mM triethanolamine buffer pH 7.5 containing 1 mM EDTA, 1 mM PMSF, 1 mM dithiothreitol and applied (flow rate 3 ml/min) on a column prepacked with DEAE-Sepharose Fast Flow gel (20 ml) and equilibrated with the same buffer. Elution was made with 50 min linear increasing salt gradient of 0.3 M NaCl (0–100%, flow rate 5 ml/min, fraction volume—2.4 ml) and detected at 280 nm (0.1 AU). The results of anion exchange chromatography on DEAE Sepharose are shown in FIG. 2. Fractions with antiviral activity (peaks II, III and IV) were collected, mixed, vacuum dried, re-precipitated with 5 volumes of ethanol, washed twice with 70% ethanol and used for the next purification with preparative PAGE.

EXAMPLE 6

Preparative PAGE

A Mini-Protein II Electrophoresis System ("Bio-Rad") was used, 17.5% acrylamide gel (thickness 1.6 mm) and the Laemmli buffer system containing detergents—SDS or Triton X-100 or a chaotrophic agent 8 M urea. The running conditions were 200 volts with constant voltage setting and the run time approximately 1 h in a cold room. After electrophoresis, the control strip of gel was cut and stained with 0.1% Coomassie Blue R-250 in 50% methanol. After destaining with 10% ethanol and 5% acetic acid to remove background, protein bands were cut from unstained gel, homogenized with 50 mM potassium-phosphate buffer, pH 7.5, with 1 mM EDTA, 1 mM PMSF, 1% ME, 0.1% detergent (SDS or Triton X-100) and incubated overnight in a cold room with shaking. The samples were evaporated, washed twice with 70% ethanol, resuspended in 10 mM potassium-phosphate buffer pH 7.4 containing 1 mM EDTA, 1 mM PMSF, 1 mM dithiothreitol and tested as to antiviral activity.

A more effective separation of protein bands was achieved when using PAGE with SDS or 8 M urea, but in these cases the material lost its antiviral activity. The staining of gel with Coomassie Blue eliminated the activity, too. Therefore the not so effective, but non-denaturating, PAGE with Triton X-100 without staining was used for searching bioactive protein bands. After elution, one part of material was tested for antiviral activity, another analyzed for homogeneity with analytical PAGE.

EXAMPLE 7

Analytical PAGE with SDS and Triton X-100

Figure 3:
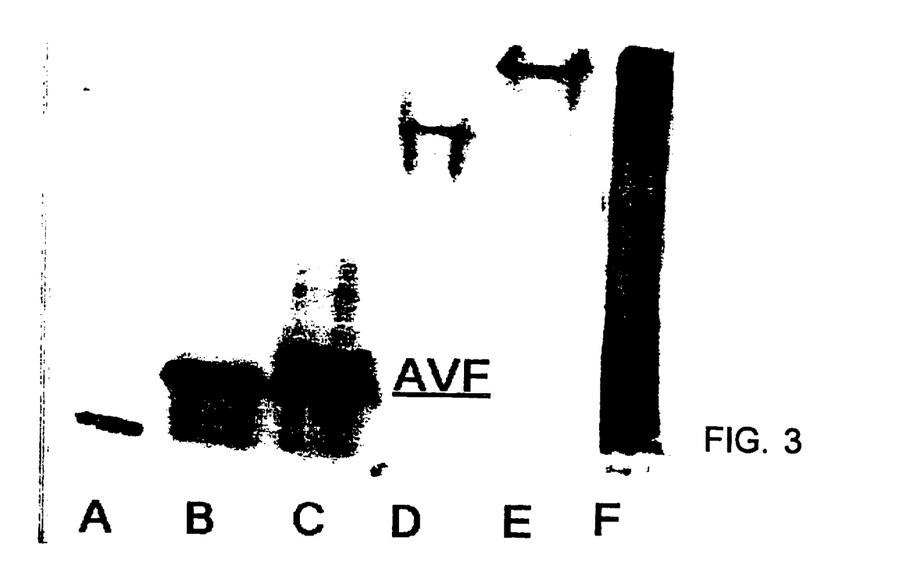
FIGS. 3 and 4 show protein bands from analytical PAGE with Triton X-100.
Figure 4:
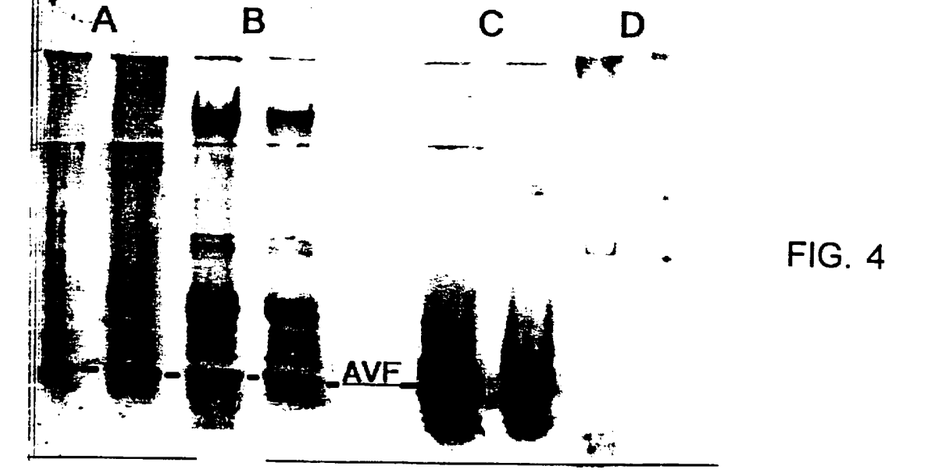
Figure 5:
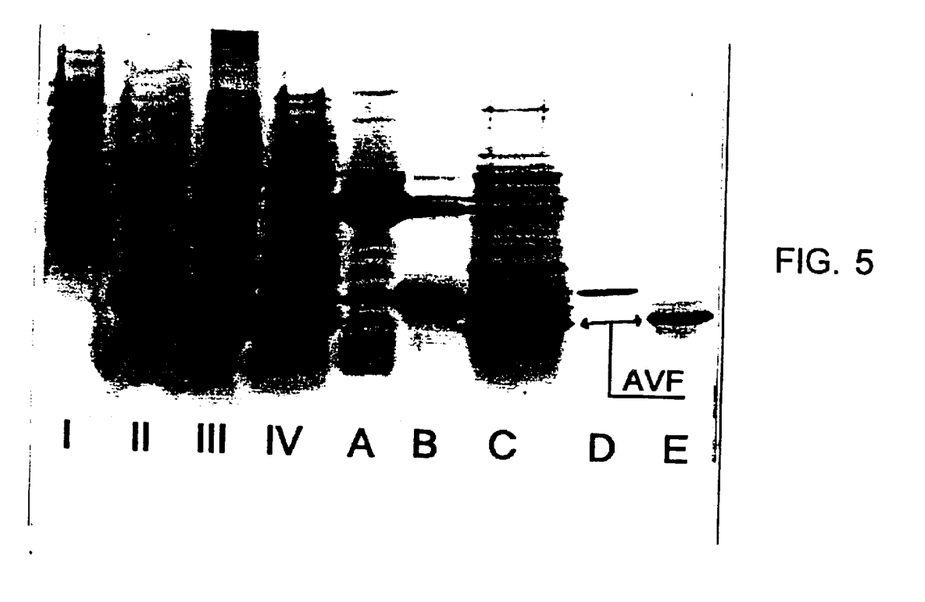
FIG. 5 shows protein bands from analytical SDS-PAGE.
Figure 6:
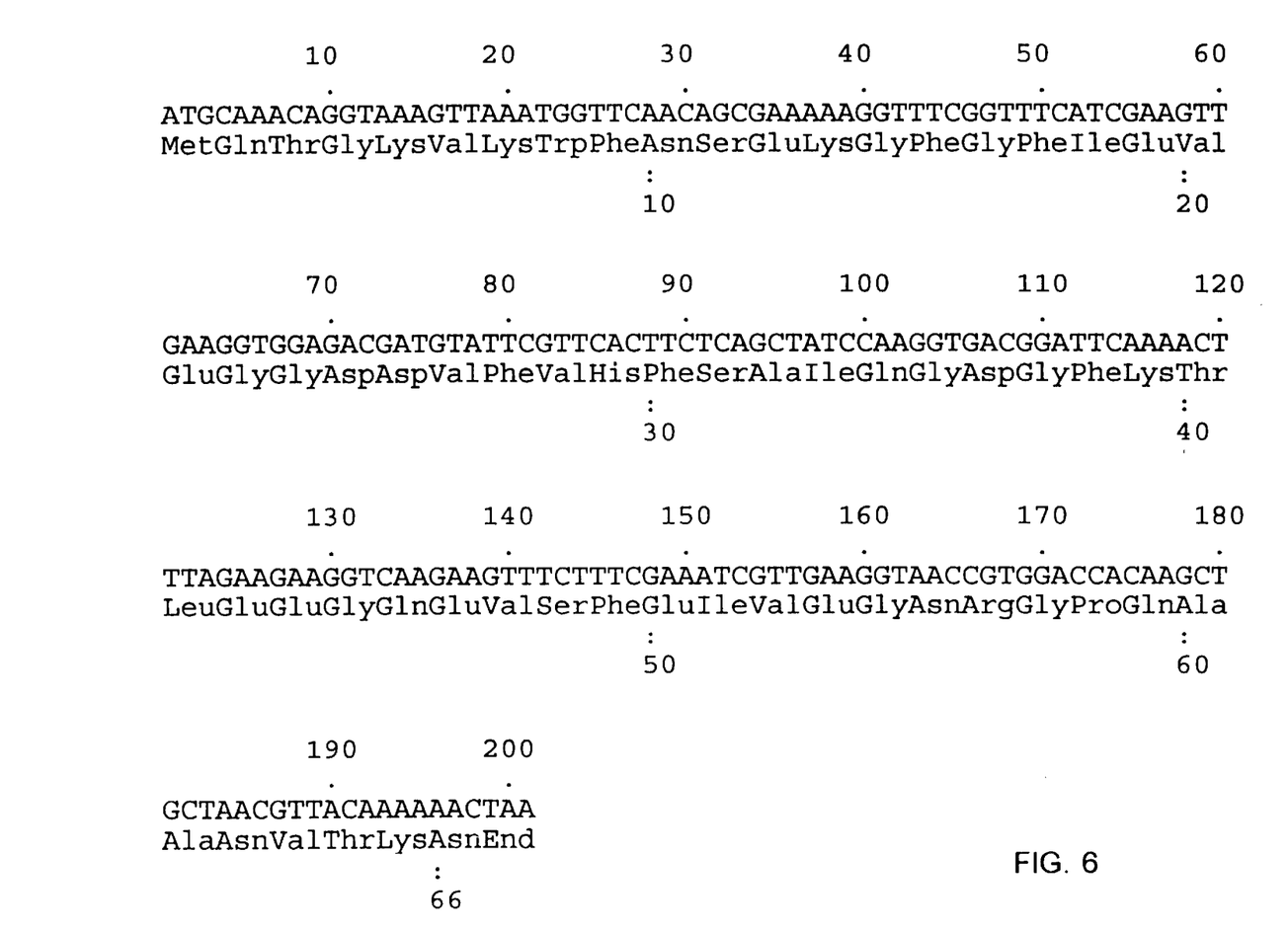
FIG. 6 shows the nucleotide and amino acid sequences of the MF2 protein from *Bacillus thuringiensis*.

A Mini-Protein II Electrophoresis System ("Bio-Rad") and the Laemmli buffer system was used. The running conditions were as those for preparative PAGE. In case of SDS, a stepwise gradient of acrylamide gel, concentrations of 5, 12.5, 15 and 17.5% was used. This method was used also for the detection of the antiviral factor at different stages of isolation and for the determination of its molecular weight. These results are shown in FIGS. 3, 4 and 5. Active sample B (FIG. 3) was evaporated and used for sequence analysis.

In FIG. 3, protein bands eluted from preparative PAGE were analyzed on 17.5% PAGE with Triton X-100. F denotes the intitial bioactive fraction after DEAE-Sepharose (FIG. 2), A to E the protein bands eluted from preparative PAGE. B, C and F are bands with antiviral activity and A, D and E are inactive bands. The symbol AVF denotes the antiviral factor MF2.

In FIG. 4, protein peaks eluted from the DEAE-Sepharose column were analyzed. F denotes the initial bioactive fraction after DEAE-Sepharose. D denotes peak I, A peak II, B peak III and C peak IV. A, B and C are peaks with antiviral activity, D is inactive.

FIG. 5 shows an analytical SDS-PAGE. A stepwise gradient of acrylamide gel concentration of 5, 12.5, 15 and 17.5% was used. I to IV are protein peaks eluted from DEAE-Sepharose, A is carbonic anhydrase (MW 29,000), B is Cytochrome C (MW=12,400), C is active fraction from DEAE-Sepharose column, D to E are protein bands eluted from preparative PAGE. II, IV, C and E are bands with antiviral activity, I and D are inactive bands.

TABLE 3

Antiviral activity at different stages of MF2 purification

| Preparation | Quantity of infective spots experiment/control (three replications) | | |
|---|---|---|---|
| 1. Alive bacterium, washed twice with water | 102/96 | 112/120 | 45/36 |
| 2. Culture filtrate | 60/85 | 62/96 | 84/120 |

TABLE 3-continued

Antiviral activity at different stages of MF2 purification

| Preparation | Quantity of infective spots experiment/control (three replications) | | |
|---|---|---|---|
| 3. Boiled extract | 17/54 | 62/145 | 44/110 |
| 4. Propanol precipitation | | | |
| 2 volumes of propanol | 16/120 | 0/40 | 14/102 |
| 5 volumes of propanol | 0/62 | 2/112 | 3/110 |
| 5. Mixture of peaks (II–IV) after DEAE-Sepharose | 14/268 | 15/293 | 10/223 |
| 6. MF2 after preparative PAGE (50 ng/ml)* | 0/52 | 2/55 | 3/70 |

*This is minimal active concentration of protein. Initial amount of protein, eluted from the gel (about 10 μg), was determined by Bredford's (1976) method and then it was diluted several times.

Conclusion

We have isolated from bacterium *B. thuringiensis* a factor which can protect tobacco plants against TMV infection. This factor has protein nature and approximate molecular weight of 8,000. It is a thermostable peptide but in a raw extract very quickly looses activity (2 h at the room temperature) which may be the result of protease activity. This proposition was confirmed by the increase of antiviral activity during purification (see Table 3). MF2 lost its antiviral activity after treatment with SDS or urea. It could be concluded that the antiviral activity of this protein depends on its structure.

Protective Properties of MF2 Preparations Against Fungal Diseases

EXAMPLE 8

Antiblast Activity of MF2

Fungus

A natural isolate H-5-3 of *Pyricularia oryzae* Cav., rice blast disease causal agent was used. The fungus was cultivated at 28° C. on agar minimal medium containing 3 mg/ml casein hydrolysate. Spores (conidia) from 10-days-old culture were washed out with distilled water (4° C.). Mycelial impurities were removed by filtration through Miracloth (Calbiochem-Behring Corp.) and two layers of a stainless steel net (pore size 50 μm). The spore suspension was washed by double centrifugation for 15 min at 7000×g, and resuspended in distilled water. The spore concentration was counted in a hemocytometer under a microscope.

Plants

Rice *Oryza sativa* L. of cv. Sha-tiao-tsao susceptible to the above mentioned strain of fungus was used. Plants were grown up to a stage of four leaves (for about 13–15 days) in pots (10 plants per pot) in soil in a climatic chamber at RH 95%, at the temperatures of 30° C. and 23° C. during light and dark periods (12 h each), respectively. The light source (20 klux) was a 10 kW xenon lamp (DKsT-10000) with a water filter.

Inoculation and Disease Estimation

Rice plants were sprayed with a spore suspension (100,000 spores per ml, 5 ml of suspension per one pot). The treated plants were incubated for 18–24 h in a moisture chamber in dark at 23° C. and then placed under the light in the climatic chamber. The disease symptoms were observed after 10 days. To test the inoculum viability, drops of spore suspension were incubated for 15 h in a multi-well plate in the dark at 23° C. The germination of spores was then counted.

Treatment with MF2 Preparations Buffer solutions of MF2 preparations were added into inoculum (the final concentration was 50 μg of lyophilised extract per ml of spore suspension). The control samples contained equal volume of buffer.

None of the MF2 preparations at the used concentrations inhibited the germination of *P. oryzae* spores in water. On the contrary, addition of the preparations to the inoculum protected the rice plants from the blast disease to a significant degree (Table 4).

TABLE 4

Antiblast activity of MF2 preparations from *B. thuringiensis*

| Bacterial preparation | Protein (μg/ml) | Number of plants (unit) | Number of infected plants × Type of infection* (a × b) | Disease** development (%) |
|---|---|---|---|---|
| Boiled extract | 100 | 24 | 6 × 0.1; 4 × 1; 11 × 2; 3 × 3; | 50 |
| Precipitate after | 50 | 23 | 18 × 0.1; 5 × 1; | 8.5 |
| treatment with | 20 | 23 | 1 × 0; 13 × 0.1; | 17 |
| propanol | | | 7 × 1; 2 × 2 | |
| (5 volumes) | 5 | 26 | 1 × 0; 6 × 0. 1.5 × 1 12 × 2; 2 × 3 | 46 |
| Fractions from column (elution volume 52–54 ml) | 3 | 22 | 2 × 0; 5 × 0.1; 10 × 1; 5 × 2 | 31 |
| Control | | 23 | 1 × 0.1; 4 × 1; 13 × 2; 5 × 3 | 70 |

*Type of infection was determined according to the method of Latterel (Latterel et al., 1964).
**Disease development was calculated by formula:

$$R = \sum \frac{(a \times b) \times 100}{N \times 3},$$

where
R - disease development (%);
a - number of infected plants;
b - type of infection;
N - total number of plants;
3 - highest type of infection.

EXAMPLE 9

Protective Activity of MF2 Preparations Against Potato Late Blight Disease

The test plants (potato, variety Lorkh) were five weeks old. Four leaflets of the fifth (counted from the top) fully opened leaf, for each variant, were cut and treated with MF2 extract which was added to *Phytophtora infestans* spores suspension ($10^3$ spores/ml). The final concentration of MF2 in the mixture was 50 μg of lyophilsed extract per ml of suspension.

In the control variant, potato leaves were inoculated by *Ph. infestans* spore suspension of the same concentration. Instead of MF2 extract, the same amount of buffer was added to this suspension.

Inoculum (0.5 ml per leaflet) was sprayed onto the leaf surface. After the inoculation, the leaves were placed in a moisture chamber for 2–3 days at 18–20° C.

Penetration intensity was determined by calculating of amount of lesions per $cm^2$ of leaf surface. The results of these experiments are presented in the Table 5.

TABLE 5

Amount of lesions per $cm^2$ of leaf surface of isolated potato leaves which were treated with MF2

| | | | | | |
|---|---|---|---|---|---|
| Control variant | 2.5 | 2.2 | 1.05 | 1.9 | 1.91 ± 0.62 |
| Experimental variant | 0.02 | 0.08 | 0.10 | 0.001 | 0.05 ± 0.047 | m ± (P = 0.95)

The results of Table 5 show a high protective activity of MF2 extract against Potato late blight disease. As no inhibitory effect of MF2 (in the used concentrations) on spore germination was found, it seems that the protective activity concerns mechanisms of induced resistance.

EXAMPLE 10

Sequencing of the N-terminus of MF2

The salts from the purest fraction of MF2 protein sample were removed by using a Pro Spin-cartridge (Applied Biosystems) according to the instructions of the manufacturer.

$NH_2$-terminal amino acid sequence analysis was performed with an Applied Biosystems model 477A protein sequencer equipped with an on-line Applied Biosystems model 120A PTH amino acid analyzer. Standard cycle parameters were used. The amino acid sequence of the N-terminus of MF2 is shown in the Table 6.

TABLE 6

MF2 protein's N-terminal sequence

| | | |
|---|---|---|
| 1. | Met | (M) |
| 2. | Gln | (Q) |
| 3. | Thr | (T) |
| 4. | Gly | (G) |
| 5. | Lys | (K) |
| 6. | Val | (V) |
| 7. | Lys | (K) |
| 8. | Thr | (W) |
| 9. | Phe | (F) |
| 10. | Asn | (N) |
| 11. | Ser | (S) |
| 12. | Glu | (E) |
| 13. | Lys | (K) |
| 14. | Gly | (G) |
| 15. | Phe | (F) |
| 16. | Xaa | (X) |
| 17. | Phe | (F) |
| 18. | Ile | (I) |
| 19. | Glu | (E) |
| 20. | Val | (V) |

EXAMPLE 11

Cloning and Sequencing of the MF2 Gene from *B. thuringiensis*

According to the N-terminal amino acid sequence, degenerated oligonucleotide 5'-ATGCA(A/G)ACIGGIAA(A/G)GTIAA(A/G)TGGTT(T/C)AA(T/C)-3' was synthesized. High-molecular-weight chromosomal DNA was isolated from *B. thuringiensis* cells and digested with 8 restictases (BamHI, EcoRI HindIII, SalI, SacI, PstI, SphI and NdeI), separately and in pairs. Restriction products were separated according to molecular weights with agarose gel electrophoresis and transferred to HybondN-membrane by a blotting procedure. Synthetic oligonucleotide was labeled with T4-polynucleotide kinase and [-$^{32}$P]ATP and used as the radioactive probe in Southern hybridization experiments. Only one positive band per restriction appeared on the X-ray films. Based on the molecular weights of positively hybridized fragments, the restriction map of the chromosomal gene of MF2 was constructed. PstI digestion of chromosomal DNA was loaded on 0.65% low-gelling agarose and after electrophoresis, DNA fragments of approximately 5.6 kbp were isolated from the gel. They were further digested with HindIII and BamHI, loaded on 0.8% low-gelling agarose gel, and after electrophoresis, DNA fragments approximately 1.6–1.7 kbp were isolated. They were ligated into vector pUC18 digested with HindIII and BamHI. Competent *E.coli* cells (strain XL1-blue) were transformed with this ligation mixture and were grown on LB-plates, containing ampicillin (50 mg/l). Colonies were transferred onto HybondN-membrane and subjected to colony hybridization procedure, with the radioactive oligonucleotide as the probe. About 70% of the colonies showed a positive hybridization.

Plasmid DNA from a positive clone was isolated and used for the sequencing of insert. The DNA sequence encoding the N-terminus of antiviral protein appeared to be near HindIII site. Open reading frame of 198 bp, started with ATG and finished with TAA, was found. According to the DNA coding region, the antiviral protein consists of 66 amino acid residues (FIG. 6.). The calculated molecular weight is 7239 D, the calculated isoelectric point is 4.43, and the molar absorptivity is 5690.

In this example the introduction of the *B. thuringiensis* gene of MF2 in the cloning vector for *E. coli* is described.

Using synthetic oligonucleotides or natural restriction sites, the gene can be introduced under the control of regulatory elements of transciption and translation specific for the organism in question, according to Sambrook et al. (1989).

EXAMPLE 12

Expression of the MF2 Gene in *E. coli*

Expression of the MF2 gene in *E. coli* was achieved as follows. Plasmid DNA containing the MF2 gene as a part of the 1.6–1.7 kbp fragment from *B. thuringiensis* (described in Example 11) was digested with retrictases HindIII and Sau3AI. To introduce the MF2 gene under the control of *E. coli* lac-promoter, the HindIII-Sau3AI fragment of about 600 bp containing the MF2 gene was isolated from 1% low-gelling agarose gel and ligated into vector pUC19 digested with HindIII and BamHI. Competent *E. coli* cells (strain XL1-blue) were transformed with this ligation mixture and were grown on LB agar containing ampicillin (50 mg/l). The plasmid obtained was designated as pBTR-31.

*E. coli* XL1-blue cells harboring pBTR-31 were grown overnight at 37° C. in LB media with ampicillin (70 mg/l). Disruption of cells and partial fractionation of soluble cell proteins was carried out as described in Example 4. Protein preparation obtained was analysed by means of 17.5% PAGE containing Triton X-100 as described in Example 7. The protein band was revealed which corresponded to authentic MF2 in molecular mass and electrophoretic properties.

The protein revealed by analytical PAGE electrophoresis was isolated preparatively as described in Example 6 and tested for an antiviral (TMV) activity on tobacco plant leaves as described in Example 2. The results shown in Table 7 demonstrates that recombinant MF2 has protective effect on tobacco plants form TMV infection comparable with the properties of native *B. thuringiensis MF*2.

TABLE 7

Antiviral activity of recombinant MF2 on tobacco plants (var. Xanthy)
Number of lesions on by MF2 treated half of the leaves/untreated half of the leaves

| Native MF2 from *B. thuringiensis* | | | Recombinant MF2 | | |
|---|---|---|---|---|---|
| 59/111 | 28/43 | 20/46 | 41/91 | 45/150 | 102/205 |

REFERENCES de Barjac H. and A. Bonnefoi. 1967. A classification of strains of *Bacillus thuringiensis* Berliner with a key to their differentiation. // J. Invertebr. Pathol. 11, P. 335–347.

Baulcombe D. 1994. Novel strategies for engineering virus resistance in plants. // Current Opinion in Biotechnology. V. 5, n. 2, P. 117–124.

Bredford M. 1976. A rapid and sensitive method for the quantitation of microgram quantities of protein utilizing the principle of protein-dye binding // Anal. Biochem. V.72. P.276–287.

Laemmli, U. K. 1970. Cleavage of structural proteins during the assembly of the head of bacteriophage T4,// Nature, V. 227, p.680–685.

Latterell F. M., Marchetti M. A., Grove B. R. 1964. Co-ordination of effort to establish an international system for race identification in *Pyricularia oryzae* // The Rice Blast Disease. Baltimor, Md.: The Johns Hopkins Press: P. 257–268.

Lee S. J., Xie A., Jiang W., Etchegaray J.-P., Jones P. G. and Inouye M. 1994. Family of the major cold-shock protein, CspA (CS7.4), of *Escherichia coli,* whose members show a high sequence similarity with the eukariotic Y-box binding proteins. // Molecular Microbiology, 11 (5), P. 833–839.

Krieg A. 1968. A taxonomic study of *Bacillus thuringiensis* Berliner.// J. Invertebr. Pathol. 12, P. 366–378.

Sambrook J., Fritsch E. F. and Maniatis T., 1989. Molecular cloning, Cold Spring Harbor Laboratory Press.

Schröder K., Zuber P., Williamsky G., Wagner B. and Marahiel M. A .1993. Mapping of the *Bacillus subtilis* csp B gene and cloning of its homologs in thermophilic, mesophilic and psychrotrophic bacilli. // Gene, 136, 277–280. The shorter Bergey's manual of determinative bacteriology // The Williams and Wilkins Company, Baltimore. Ed. by Holt. 1980. P.495.

Williamsky G., Bang H., Fisher G., Marahiel M. A., Characterization of csp B, a *Bacillus subtilis*-inducible cold shock gene affecting cell viability at low temperatures.// J. Bacteriol. 174: 6326–6335 (1992).

What is claimed is:

1. An isolated DNA comprising a nucleotide sequence encoding a polypeptide comprising an amino acid sequence identified as SEQ ID NO: 2, or encoding a fragment of said polypeptide with an antiviral and/or antifungal activity characteristic of the polypeptide comprising the amino acid sequence identified as SEQ ID NO: 2.

2. The DNA according to claim 1, wherein said nucleotide sequence is (a) the DNA sequence identified as SEQ ID NO: 1 or a fragment thereof, wherein said fragment encodes a polypeptide having antiviral and/or antifungal activity, or (b) a DNA sequence which has degenerate codons with respect to the DNA sequence encoding the polypeptide comprising the amino acid sequence identified as SEQ ID NO:2 or a fragment thereof, wherein said fragment has antiviral and/or antifungal activity.

3. A vector comprising the DNA according to claim 1 or 2.

4. A host cell stably transformed or transfected with a vector according to claim 3.

5. A transgenic plant comprising a vector according to claim 3, wherein the plant expresses the polypeptide encoded by the DNA.

6. A transgenic plant according to claim 5 that is a tobacco or potato plant.

7. An isolated DNA according to claim 1, wherein the DNA further comprises a heterologous promoter operatively linked to the polypeptide-encoding sequence to promote expression in plant cells.

8. A transgenic plant comprising a DNA according to any one of claims 1, 2, or 7, wherein the plant expresses the polypeptide encoded by the DNA.

9. The transgenic plant of claim 8, wherein the plant is resistant to at least one phytopathogen selected from the group consisting of Tobacco Mosaic Virus, Potato Virus X, *Phytophtora infestans,* and *Pyricularia oryzae.*

10. A transgenic plant according to claim 8 that is a tobacco or potato plant.

11. An isolated polynucleotide comprising a nucleotide sequence encoding a polypeptide having an amino acid sequence identified as SEQ ID NO: 2.

12. A host cell stably transformed or transfected with a polynucleotide according to claim 1 or 11.

13. An isolated polypeptide comprising an amino acid sequence identified as SEQ ID NO: 2 or a fragment of said polypeptide having antiviral and/or antifungal activity characteristic of a polypeptide comprising the amino acid sequence identified as SEQ ID NO: 2.

14. A method of isolating and purifying the polypeptide as defined in claim 13 from bacterial cells expressing said polypeptide, which method comprises
    (a) extracting the bacterial cells with an appropriate buffer solution by heating to an elevated temperature in order to eliminate temperature sensitive substances from an extraction medium,
    (b) precipitating a crude polypeptide at low temperature with an appropriate precipitant to eliminate lower molecular weight organic substances from a protein fraction,
    (c) fractionating a suspension of the precipitate comprising the polypeptide of step (b) through an anion exchange chromatography column, and collecting fractions having antiviral or antifungal activity,
    (d) performing polyacrylamide gel electrophoresis (PAGE) to the polypeptide fractions having antiviral or antifungal activity, and
    (e) recovering an isolated polypeptide eluted from the gel of step (d).

15. The method according to claim 14, wherein the bacterial cells are from *Bacillus thuringiensis.*

16. The method according to claim 14 wherein the heating in step (a) takes place in a boiling water bath.

17. The method according to claim 16, wherein the bacterial cells are extracted with a potassium-phosphate buffer at pH 7.4 containing EDTA, PMSF, mercaptoethanol and Triton X-100.

18. The method according to any one of claims 14 to 17, wherein the precipitation in step (b) takes place at approximately 2 to 6° C. with cool chloroform and/or propanol and/or ammonium sulphate solution.

19. A plant protectant which comprises the polypeptide as defined in claim 13.

20. A plant protectant composition which comprises the polypeptide as defined in claim 13, and further comprises a carrier or additive.

21. A method for induction of plant resistance to viral or fungal phytopathogens, which comprises applying to plants a plant protecting amount of a plant protectant according to claim 19 or a plant protectant composition according to claim 20.

22. A method of protecting a plant or plant culture from viral or fungal phytopathogens comprising the step of:
    contacting a plant or plant culture with a plant-protecting amount of a polypeptide according to claim 13.

23. A method according to claim 22 wherein said contacting step comprises including said polypeptide in a plant culture medium.

24. A method of protecting a plant or plant culture from at least one viral phytopathogen selected from the group consisting of Tobacco Mosaic Virus (TMV) and Potato Virus X (PVX), comprising the step of:
    contacting a plant or plant culture with a polypeptide according to claim 13 in an amount effective to render protection against at least one of said TMV and PVX.

25. A method according to claim 24 wherein said plant or plant culture is selected from the group consisting of tobacco and potato.

26. A method of protecting a plant or plant culture from the phytopathogen *Phytophtora infestans* comprising the step of:
    contacting a plant or plant culture that is susceptible to the phytopathogen *Phytophtora infestans* with a polypeptide according to claim 13 in an amount effective to render protection against *Phytophtora infestans.*

27. A method of protecting a rice plant or plant culture from rice blast disease caused by the phytopathogen *Pyricularia oryzae* comprising the step of:
    contacting a rice plant or plant culture that is susceptible to the phytopathogen *Pyricularia oryzae* with a polypeptide according to claim 13 in an amount effective to render protection against rice blast disease caused by *Pyricularia oryzae.*

28. A method of purifying the polypeptide according to claim 13 from cells expressing said polypeptide comprising the steps of:
    (a) heating a suspension of the cells to disrupt the cells and inactivate temperature sensitive proteases;
    (b) precipitating a crude protein resulting from step (a) with a precipitant to separate lower molecular weight organic substances from the polypeptide;
    (c) fractionating the polypeptide from step (b) via chromatography; and
    (d) collecting fractions having antiviral and/or antifungal activity.

29. The method according to claim 28, wherein the cells expressing the polypeptide are bacterial cells.

30. The method according to 28, wherein the precipitation in step (b) takes place at approximately 2 to 6° C., and wherein the precipitant comprises a member selected from the group consisting of chloroform, propanol, ammonium sulphate, and mixtures thereof.

31. A purified polypeptide comprising an amino acid sequence identified as SEQ ID NO: 2.

32. A composition for application to a plant comprising a polypeptide according to claim 31.

33. A method for induction of plant resistance to viral or fungal phytopathogens, which comprises applying to plants a plant protecting amount of a polypeptide according to claim 31 or a composition according to claim 32.

34. A method of purifying a thermostable, phytopathogen-resistance conferring, non-phytotoxic polypeptide from *Bacillus thuringiensis* cells expressing said polypeptide, comprising the steps of:
    (a) heating a suspension of the cells to disrupt the cells and inactivate temperature sensitive proteases;
    (b) precipitating crude protein resulting from step (a) at approximately 2–6° C. with a precipitant to separate lower molecular weight organic substances from polypeptides in the crude protein;
    (c) fractionating the polypeptides from step (b) via chromatography; and (d) recovering a purified, thermostable, phytopathogen-resistance conferring, non-phytotoxic polypeptide by collecting fractions having antiviral and/or antifungal activity.

35. The method according to claim 34, wherein the suspension of step (a) comprises the cells to be disrupted, and further comprises potassium-phosphate buffer, EDTA, PMSF, mercaptoethanol and Triton X-100.

36. The method according to 34, wherein the precipitation in step (b) takes place at approximately 2 to 6° C., and wherein the precipitant comprises a member selected from the group consisting of chloroform, propanol, ammonium sulphate, and mixtures thereof.

37. A method according to claim 34 further comprising a step, after said heating step, of centrifuging the suspension to separate cellular precipitates from a supernatant comprising crude protein.

38. A method of isolating a thermostable, antiviral and/or antifungal protein from *Bacillus thuringiensis* cells expressing said protein, comprising steps of:

heating a suspension of the cells to disrupt the cells and inactivate temperature sensitive proteases;

centrifuging the suspension after the heating step to separate contaminants from a supernatant containing crude protein; and precipitating protein in the supernatant to separate the protein from lower molecular organic substances, thereby isolating a thermostable protein with antiviral and/or antifungal activity.

39. The method according to claim 38, wherein the suspension further comprises a potassium-phosphate buffer containing EDTA, PMSF, mercaptoethanol and Triton X-100, and wherein the suspension is heated to temperature of boiling water.

40. The method according to claim 39, wherein the precipitating step comprises treating the supernatant with chloroform at approximately 2 to 6° C. to precipitate the protein.

41. The method according to claim 40, further comprising treating the precipitated protein with propanol after the chloroform precipitation.

* * * * *

SEQUENCE LISTING

<160> NUMBER OF SEQ ID NOS: 2

<210> SEQ ID NO 1
<211> LENGTH: 201
<212> TYPE: DNA
<213> ORGANISM: Bacillus thuringiensis
<220> FEATURE:
<221> NAME/KEY: CDS
<222> LOCATION: (1)..(201)

<400> SEQUENCE: 1

```
atg caa aca ggt aaa gtt aaa tgg ttc aac agc gaa aaa ggt ttc ggt       48
Met Gln Thr Gly Lys Val Lys Trp Phe Asn Ser Glu Lys Gly Phe Gly
  1               5                  10                  15 ttc atc gaa gtt gaa ggt gga gac gat gta ttc gtt cac ttc tca gct       96
Phe Ile Glu Val Glu Gly Gly Asp Asp Val Phe Val His Phe Ser Ala
             20                  25                  30 atc caa ggt gac gga ttc aaa act tta gaa gaa ggt caa gaa gtt tct      144
Ile Gln Gly Asp Gly Phe Lys Thr Leu Glu Glu Gly Gln Glu Val Ser
         35                  40                  45 ttc gaa atc gtt gaa ggt aac cgt gga cca caa gct gct aac gtt aca      192
Phe Glu Ile Val Glu Gly Asn Arg Gly Pro Gln Ala Ala Asn Val Thr
     50                  55                  60 aaa aac taa                                                          201
Lys Asn
 65

<210> SEQ ID NO 2
<211> LENGTH: 66
<212> TYPE: PRT
<213> ORGANISM: Bacillus thuringiensis

<400> SEQUENCE: 2

Met Gln Thr Gly Lys Val Lys Trp Phe Asn Ser Glu Lys Gly Phe Gly
  1               5                  10                  15

Phe Ile Glu Val Glu Gly Gly Asp Asp Val Phe Val His Phe Ser Ala
             20                  25                  30

Ile Gln Gly Asp Gly Phe Lys Thr Leu Glu Glu Gly Gln Glu Val Ser
         35                  40                  45

Phe Glu Ile Val Glu Gly Asn Arg Gly Pro Gln Ala Ala Asn Val Thr
     50                  55                  60

Lys Asn
 65
```